US00PP28446P3

(12) United States Plant Patent
Kearley, Jr.

(10) Patent No.: US PP28,446 P3
(45) Date of Patent: Sep. 26, 2017

(54) ***MANDEVILLA* PLANT NAMED 'FGRRV1'**

(50) Latin Name: *Mandevilla splendens*
Varietal Denomination: FGRRV1

(71) Applicant: Richard C. Kearley, Jr., Hawthorne, FL (US)

(72) Inventor: Richard C. Kearley, Jr., Hawthorne, FL (US)

(73) Assignee: FURY GENETICS LLC, Hawthorne, FL (US)

( * ) Notice: Subject to any disclaimer, the term of this patent is extended or adjusted under 35 U.S.C. 154(b) by 30 days.

(21) Appl. No.: 14/998,427

(22) Filed: Dec. 31, 2015

(65) Prior Publication Data

US 2017/0196140 P1 Jul. 6, 2017

(51) Int. Cl.
*A01H 5/02* (2006.01)

(52) U.S. Cl.
USPC ..... Plt./232

(58) Field of Classification Search
USPC ..... Plt./232
See application file for complete search history.

*Primary Examiner* — Keith Robinson
(74) *Attorney, Agent, or Firm* — C. A. Whealy

(57) ABSTRACT

A new and distinct cultivar of *Mandevilla* plant named 'FGRRV1', characterized by its upright and somewhat outwardly spreading to strongly vining plant habit; medium green and creamy white variegated leaves that are initially tinged with red; red purple-colored flowers; and good garden performance.

3 Drawing Sheets

Botanical designation: *Mandevilla splendens.*
Cultivar denomination: 'FGRRV1'.

BACKGROUND OF THE INVENTION

The present invention relates to a new and distinct cultivar of *Mandevilla* plant, botanically known as *Mandevilla splendens* and hereinafter referred to by the name 'FGRRV1'.

The new *Mandevilla* plant is a naturally-occurring branch mutation of *Mandevilla splendens* 'Red Riding Hood', not patented. The new *Mandevilla* plant was discovered and selected by the Inventor on a single plant within a population of plants of 'Red Riding Hood' grown in a controlled greenhouse environment in Hawthorne, Fla. in May, 2012. The selection of the new *Mandevilla* was based on its variegated leaves.

Asexual reproduction of the new *Mandevilla* plant by tip cuttings in a controlled greenhouse in Hawthorne, Fla. since July, 2012 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'FGRRV1'. These characteristics in combination distinguish 'FGRRV1' as a new and distinct *Mandevilla* plant:

1. Upright and somewhat outwardly spreading to strongly vining plant habit.

2. Medium green and creamy white variegated leaves that are initially tinged with red.
3. Red purple-colored flowers.
4. Good garden performance.

Plants of the new *Mandevilla* differ primarily from plants of the mutation parent, 'Red Riding Hood', in leaf color as plants of 'Red Riding Hood' have solid green-colored leaves.

Plants of the new *Mandevilla* can be compared to plants of the *Mandevilla splendens* 'FGVR2', disclosed in U.S. Plant Pat. No. 25,814. In side-by-side comparisons conducted in Hawthorne, Fla., plants of the new *Mandevilla* differed from plants of 'FGVR2' in the following characteristics:

1. Plants of the new *Mandevilla* were vigorous than plants of 'FGVR2'.
2. Plants of the new *Mandevilla* had longer internodes than plants of 'FGVR2'.
3. Plants of the new *Mandevilla* had larger leaves than plants of 'FGVR2'.
4. Plants of the new *Mandevilla* had variegated leaves whereas plants of 'FGVR2' had solid green-colored leaves.
5. Plants of the new *Mandevilla* had red purple-colored flowers whereas plants of 'FGVR2' had dark red-colored flowers.

Plants of the new *Mandevilla* can be compared to plants of the *Mandevilla splendens* 'FGVP1', disclosed in U.S. Plant Pat. No. 26,001. In side-by-side comparisons conducted in Hawthorne, Fla., plants of the new *Mandevilla* differed from plants of 'FGVP1' in the following characteristics:

1. Plants of the new *Mandevilla* were vigorous than plants of 'FGVP1'.
2. Plants of the new *Mandevilla* had longer internodes than plants of 'FGVP1'.

3. Plants of the new *Mandevilla* had larger leaves than plants of 'FGVP1'.
4. Plants of the new *Mandevilla* had variegated leaves whereas plants of 'FGVP1' had solid green-colored leaves.
5. Plants of the new *Mandevilla* had red purple-colored flowers whereas plants of 'FGVP1' had pink-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical plant of 'FGRRV1' grown in a container.

The photograph on the second sheet is a close-up view of typical leaves of 'FGRRV1'.

The photograph on the third sheet is a close-up view of a typical flower of 'FGRRV1'.

DETAILED BOTANICAL DESCRIPTION

Plants used for the aforementioned photographs and following description were grown during the spring and summer in 2-gallon containers in an outdoor nursery in Fort Worth, Tex. and under cultural practices which closely approximate commercial production conditions. During the production of the plants, day temperatures ranged from 24° C. to 38° C. and night temperatures ranged from 21° C. to 24° C. Plants were 18 months old when the photographs and description were taken. In the following description, color references are made to The Royal Horticultural Society Colour Chart, 2007 Edition, except where general terms of ordinary dictionary significance are used.

Botanical classification: *Mandevilla splendens* 'FGRRV1'.

Parentage: Naturally-occurring branch mutation of *Mandevilla splendens* 'Red Riding Hood', not patented.

Propagation:

*Type*.—By tip cuttings.

*Time to initiate roots, summer*.—About 18 days at temperatures about 27° C.

*Time to initiate roots, winter*.—About three weeks at temperatures about 24° C.

*Time to produce a rooted young plant, summer*.—About 45 days at temperatures about 27° C.

*Time to produce a rooted young plant, winter*.—About 50 days at temperatures about 21° C.

*Root description*.—Fibrous, medium in thickness; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Initially upright to somewhat outwardly spreading and strongly vining plant habit; vigorous growth habit.

*Plant height*.—About 48 cm.

*Plant diameter* (*spread*).—About 67.5 cm.

*Lateral branch description*.—Length: About 42 cm. Diameter: About 4 mm. Internode length: About 2 cm to 5.5 cm. Strength: Flexible, strong. Texture, young stems: Smooth, glabrous. Texture, developing stems: Smooth, glabrous. Texture, developed stems: Woody. Luster, young stems: Glossy. Luster, developing stems: Slightly glossy. Luster, developed stems: Dull. Color, young stems: Close to 145A. Color, developing stems: Close to 175A. Color, woody stems: Close to 183A.

Leaf description:

*Arrangement*.—Opposite, simple.

*Length*.—About 5.9 cm.

*Width*.—About 4 cm.

*Shape*.—Elliptic to ovate.

*Apex*.—Acute to cuspidate.

*Base*.—Obtuse with cordate tendencies.

*Margin*.—Entire.

*Texture, upper and lower surfaces*.—Smooth, glabrous; leathery.

*Luster, upper surface*.—Somewhat glossy.

*Luster, lower surface*.—Slightly glossy.

*Venation pattern*.—Pinnate.

*Color*.—Developing leaves, upper and lower surfaces: Center, random sectors, close to 147B and 147C; towards the margins, random sectors, close to 158B to 158D; entire surface overlain with close to 58B; midvein, close to 58A and 58B; lateral venation, similar to lamina coloration. Fully expanded leaves, upper and lower surfaces: Center, random sectors, close to 147B and 147C and 148C; towards the margins, random sectors, close to 158B to 158D; thin margins, close to 58B; midvein, close to 158B to 158D; lateral venation, similar to lamina coloration.

*Petioles*.—Length: About 2 cm. Diameter: About 2 mm. Texture, upper and lower surfaces: Smooth, glabrous. Color, upper and lower surfaces: Close to 158B to 158D.

Flower description:

*Flower type and habit*.—Single salverform flowers; flowers arranged in terminal and axillary clusters; flowers face mostly outwardly; freely flowering habit.

*Natural flowering season*.—Plants of the new *Mandevilla* flower continuously year-round in Florida.

*Flower longevity on the plant*.—Flowers last about five to ten days depending on ambient temperature; flowers not persistent.

*Fragrance*.—None detected.

*Flowers*.—Appearance: Flared trumpet, corolla fused, five-parted; flowers salverform and roughly star-shaped. Diameter: About 6 cm to 8.5 cm. Depth (length): About 4 cm to 5.5 cm. Throat diameter: About 1.5 cm. Tube length: About 3.4 cm. Tube diameter, base: About 4.5 mm.

*Flower buds*.—Length: About 3.6 cm. Diameter: About 4 mm. Shape: Cylindrical, pointed. Color: Towards the base and apex, close to N57A; mid-section, close to 155B.

*Corolla*.—Arrangement: Single whorl of five petals, fused into flared trumpet; petals reflexing. Petal lobe length: About 2.25 cm to 3.5 cm. Petal lobe width: About 2 cm to 3 cm. Petal lobe shape: Roughly spatulate. Petal apex: Acute. Petal margin: Entire; undulate. Petal texture, upper and lower surfaces:

Smooth, glabrous; velvety. Throat and tube texture: Smooth, glabrous. Color: Petal, when opening and fully opened, upper surface: Close to N57A; towards the base, small spot, close to NN155B. Petal, when opening and fully opened, lower surface: Close to N57A. Throat: Close to 9A. Tube: Close to 155B; towards the base, close to N57A.

*Sepals*.—Arrangement and appearance: Five per flower in a single whorl; fused towards the base. Length: About 7 mm to 10 mm. Width: About 2.5 mm to 3 mm. Shape: Lanceolate. Apex: Acute; reflexed. Margin: Entire. Texture, inner and outer surfaces: Smooth, glabrous. Color, inner surface: Close to 145B. Color, outer surface: Close to 144A.

*Peduncles*.—Length: About 1.5 cm. Diameter: About 2.5 mm. Texture: Smooth, glabrous. Strength: Flexible, but strong. Aspect: Initially upright, becoming more outwardly arching with the weight of the developing flower. Color: Close to 144B.

*Reproductive organs*.—Stamens: Quantity and arrangement: Typically five; filaments fused to corolla; anthers, connivent. Filament length: About 1 cm to 2 cm. Filament color: Close to 155D. Anther shape: Elongated oblong. Anther length: About 5 mm to 7 mm. Anther color: Close to 12A. Pollen amount: None observed. Pistils: Quantity: Typically one. Pistil length: About 2.5 cm. Stigma shape: Oblong to rounded. Stigma color: Close to 11D. Style length: About 2 cm. Style color: Close to 155D. Ovary color: Close to 145A to 145B.

*Seeds and fruits*.—Seed and fruit production have not been observed on plants of the new *Mandevilla*.

Disease & pest resistance: Plants of the new *Mandevilla* have not been observed to resistant to pathogens and pests common to *Mandevilla* plants.

Garden performance: Plants of the new *Mandevilla* have been observed to have good garden performance to tolerate rain, wind and temperatures from about 1° C. to about 40° C.

It is claimed:

1. A new and distinct *Mandevilla* plant named 'FGRRV1' as illustrated and described.

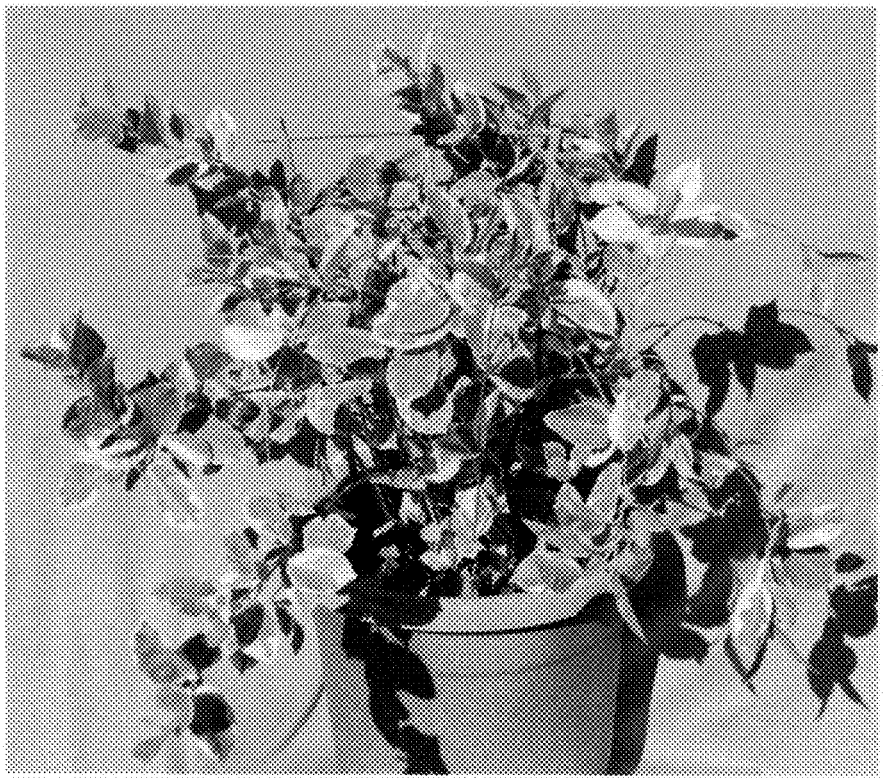

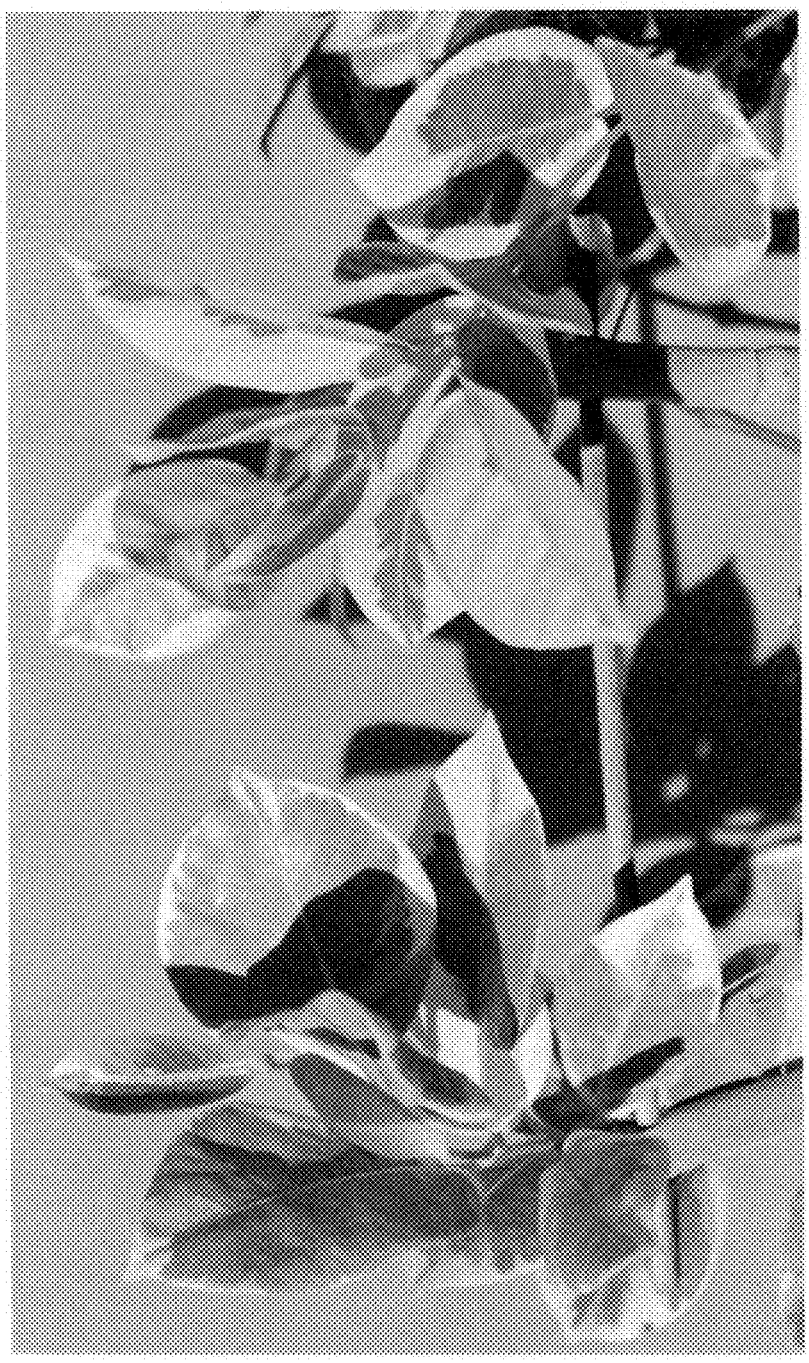

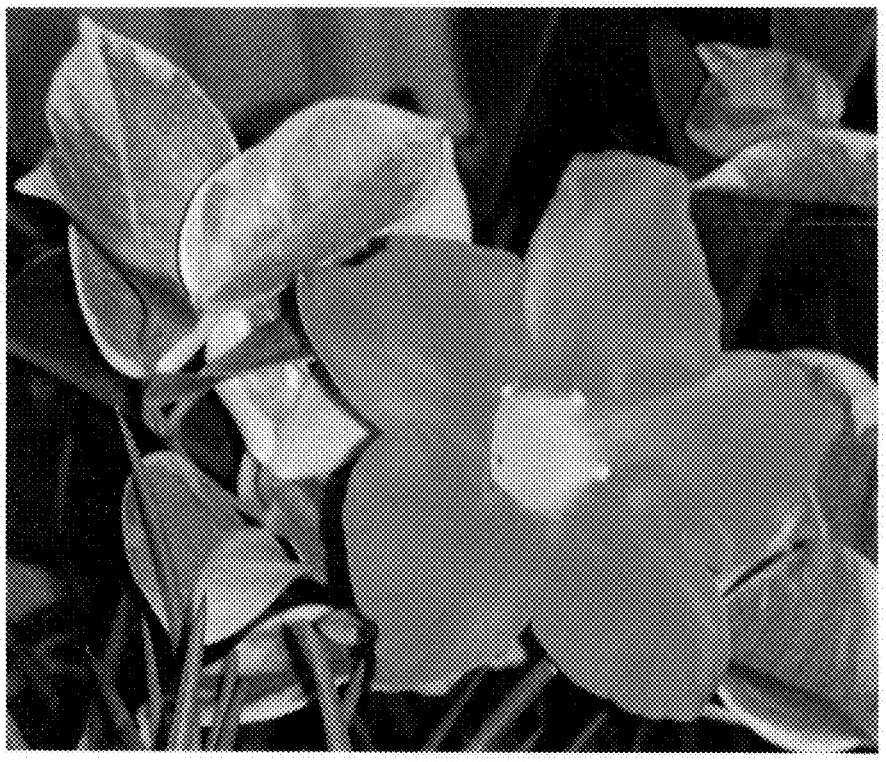

* * * * *